United States Patent [19]

Ambrus et al.

[11] Patent Number: 4,714,556

[45] Date of Patent: Dec. 22, 1987

[54] BLOOD PURIFICATION

[76] Inventors: Clara M. Ambrus, 143 Windsor Ave., Buffalo, N.Y. 14209; Csaba Horvath, 69 Pine Crest Rd., Orange, Conn. 06477

[21] Appl. No.: 711,304

[22] Filed: Mar. 13, 1985

Related U.S. Application Data

[63] Continuation-in-part of Ser. No. 406,495, Aug. 9, 1982, abandoned, and Ser. No. 650,772, Sep. 13, 1984, Pat. No. 4,612,122, which is a continuation-in-part of Ser. No. 473,814, Jun. 29, 1981, abandoned, which is a continuation-in-part of Ser. No. 278,631, Jun. 29, 1981, abandoned.

[51] Int. Cl.$^4$ .............................................. B01D 13/00
[52] U.S. Cl. .................................. 210/638; 210/321.8
[58] Field of Search ...................... 210/500.2, 632, 638, 210/648, 321.1, 321.2, 321.3

[56] References Cited

U.S. PATENT DOCUMENTS

| | | | |
|---|---|---|---|
| 3,930,105 | 12/1975 | Christen et al. | 210/500.2 X |
| 4,247,393 | 1/1981 | Wallace | 210/638 |
| 4,266,026 | 5/1981 | Breslau | 210/638 X |
| 4,323,457 | 4/1982 | Sun et al. | 210/321.1 X |
| 4,375,414 | 3/1983 | Strahilevitz | 210/648 X |

Primary Examiner—Frank Spear
Attorney, Agent, or Firm—Andrew F. Kehoe

[57] ABSTRACT

Extracorporeal apparatus for selective removal of pathogenic factors, i.e. antigens, from blood by circulating the blood through hollow fibers which, exterior to the lumen are in proximity to antibodies, i.e. proteins having strong biospecific activity for the pathogenic factors. In some situations, the antibody is segregated in a liquid medium outside the hollow fiber to improve mass transfer and the antigen penetrates the ultrafilter wall of the fiber to join the antibody.

18 Claims, 3 Drawing Figures

BLOOD PURIFICATION

RELATED APPLICATION

This application is a continuation-in-part of U.S. patent application Ser. No. 406,495 filed on Aug. 9, 1982, now abandoned, and a continuation-in-part of Ser. No. 650,772 filed on Sept. 13, 1984, now U.S. Pat. No. 4,612,126, which was itself a continuation-in-part of now abandoned Ser. No. 473,814 which was a continuation-in-part of 278,631 filed on June 29, 1981 by Clara M. Ambrus and Csaba G. Horvath.

BACKGROUND OF THE INVENTION

This invention relates to the removal of pathogenic substances from blood.

Earlier work includes the treatment of blood to remove pathogenic material by a variety of physical means including, for example, dialysis techniques and the like. Hemodialysis, however is not a sufficiently specific procedure. Also, if one removes smaller molecules such as salicylates or barbiturates by hemodialysis, the procedure is slow and incomplete, because it depends upon the concentration of the poison in the blood plasma. Larger molecules such as proteins cannot be removed by dialysis, but only by plasmapheresis and exchange-transfusion procedures. Such procedures remove more of the blood than is actually required. Thus, in plasmapheresis, there is need for replacement fluid. In exchange transfusion large amounts of blood are needed, and there remains the problem of dealing with antigens such as hepatitis virus from the transfused blood.

More recently, centrifugation of the circulating blood plasma and perfusion over an immumoabsorbent bed has been utilized, under experimental conditions, for the removal of antibodies by Protein A in cancer patients. This procedure requires a complex apparatus for the separation of plasma by centrifugation, separate passage of plasma over the absorbing bed, and subsequent reconstitution with the cellular elements of blood before returning the blood to the patient. The complexity of the process gives rise to errors, and limits its use to specific centers having equipment and necessary highly-trained technicians to operate the equipment. Also there is an undesirable risk of loss of blood components, of hemolysis, or other untoward reactions, particularly since a relatively high fraction of the patients' total blood volume is outside the body during the procedure.

A need for improved blood detoxification system has existed. The present inventors have worked to provide such a system.

OTHER ART

Processes for detoxification of blood through ultrafiltration membranes have been suggested in published art. One patent, that to Larsson et al (U.S. Pat. No. 4,361,484) suggests that such processes can be suitably accelerated by reliance on a pumping action wherein the blood is constantly pushed into and pulled out of pores in the membrane. This type of mechanical action on blood platelets, resulting in constant changes in velocity and pressure, tends to promote plating of the blood, e.g. the depositing of thrombocytes.

SUMMARY OF THE INVENTION

Therefore, it is a principal object of the present invention to provide a relatively gentle blood-treating apparatus that minimizes damage to circulating cells while selectively removing pathogenic agents, including antigens, antibodies and antibody complexes from the bloodstream.

It is a further object of the invention to provide improved means to immobilize a biologically-selective agent, exterior to the lumen surface of a hollow fiber, which will remove antigens, antigen-antibody complexes, and other harmful materials from the bloodstream.

It is another object of the invention to provide a high concentration gradient between said blood and the biologically-selective agent, thereby obtaining a faster reduction of toxins from the blood.

It is a further object of the invention to incorporate the unique selection diffusion properties of hollow fiber ultrafiltration membranes into a compact, efficient detoxification system which can be used in conjunction with instrumentation of the kind currently employed in hemodialysis by substituting the non-specific hemodialysis membrane with a cartridge containing antigen-specific immunoaborbents in combination with hollow-fiber membranes.

Other objects of the invention will be obvious to those skilled in the art on their reading of this application.

The above objects have been substantially achieved by the use of biospecific molecules, normally protein molecules called antibodies, but for some purposes antigen molecules, exterior to the lumen surface of hollow fiber tubes. These biospecific molecules and the exterior of the tubes are also in a closed-volume system so that, steady-state, there is only diffusion flow through the membrane.

The following specific embodiments of the invention are contemplated:

(1) Immobilization of an antibody exterior to the lumen surface of the hollow fiber tube. In order to make the antibody spatially "available" for contact with the antigen, it is often desirable to have a molecular spacer segment forming means for spacing the antibody from the wall of the exterior porous side of the hollow fiber membrane. This general arrangement is preferred when the molecular weight of the antigen is large, e.g., 100,000 Daltons or higher in molecular weight. A convenient range interior surface area of tubes present in a single parallel group and mounted within a single cartridge is from about 0.1 to 5 square meters. When the antigen, or toxic substance is of low molecular weight, as is the case with digoxin, quinidine, proploxyphene napsylate, barbiturates, salicylates, or theophylline, the hollow tube need only be permeable to small or medium size molecules. When the toxic substance is large, such as anti-insulin antibody, antihemophilic antibody or an immune complex such as those involved in rheumatoid arthritis, myasthenia gravis, glomerulonephritis, lupus erythematosus or other immune complex or autoimmune diseases, the pores of the lumen must be of sufficient size to allow diffusion of the antibody or immune complex but small enough to prevent passage of the smallest blood cells, the thrombocytes or blood platelets. In most cases, it will be desirable to have an interior diameter of the hollow fiber from 100 to 400 micrometers and a tubular length of 7 to 50 cm. When a particular application requires, a six- or eight-carbon methylene group is convenient as a spacer or "handle" between antibody and tube wall.

(2) Coating of the exterior porous surface of the membrane with albumin. When the antigen to be removed is readily absorbed by albumin or when the immunologically active antibody is more readily chemically reacted with albumin than with the material of the surface of the hollow fiber, the spacer molecule may be a protein such a albumin.

The outer surface of a membrane can be considered a relatively porous material compared to that of the interior surface which is normally the effective filter surface of an ultrafilter membrane of the asymmetric, sometimes called anisotropic, type. Thus, for example, the exterior, porous side of a hollow fiber membrane may be treated with a 17% human albumin solution in saline. The albumin will coat the surfaces within the porous zone of the membrane structure (i.e. the zone that underlies the barrier layer of the membrane) and, thereafter, a solution of protein (antibody) can be deposited upon the albumin. Often it is desirable to crosslink the protein somewhat (as with a dilute glutaraldehyde solution or some other such mild crosslink-inducing agent); this aids in anchoring the material in place on the hollow fiber surface.

(3) Another approach to preparing a hollow fiber cartridge which is capable of removing pathogenic factors from blood is an extracorporeal circulation system that embodies a hollow fiber cartridge with the fiber membranes having sufficient permeability for the pathogenic blood factor to be removed through the membrane and into a soluble, immobilized antibody sequestered in the extrafiber space. The term immobilization simply means the formation of a high molecular weight polymeric conjugate of the antibody that cannot cross the membrane into the lumen of the membrane. In order to form a soluble, immobilized antibody the molecular weight of the immunoreactive antibody may be increased to such a size that it will not diffuse, from the exterior, porous, portion of the hollow fiber, through the lumen and thence into the blood to be purified. This can be done by chemically reacting the antibody with a high molecular weight, water-soluble substance such as silica gel or dextran or by polymerizing the immunoreactive antibody. The use of such macromolecular-borne antibodies is advantageous for high rate of antigen absorption, due to enhanced rate of polarization effects on mass transfer and binding kinetics. Furthermore the antibody uptake by the fluid is readily monitored, e.g. by removal of aliquots of the solution for assay, during the course of treatment.

When hollow fiber cartridges are prepared for the removal of substances with high albumin affinity, such as bilirubin, it is sufficient to "immobilize" high concentration of albumin on the outer, i.e. shell, side of the hollow fiber membranes with either of the methods described above.

It wll be understood that, in the convention used in this application, the troublesome blood component is called an antigen. In some cases this troublesome component may be known to the art as an "antibody". In such cases, it will be immobilized on a substrate which is immunoreactive with it, for example an antigen or an anti-human antibody, or sequestered in any of the other ways described here as an antibody.

SOME SPECIFIC USES FOR THE INVENTION (1) Immobilization of serum albumin for the removal of excess metabolites with high albumin affinity, such as bilirubin, for the treatment of hyperbilirubinemia of hepatic origin in the neonate.

(2) Immobilization of specific antibodies for the removal of excess drugs, intoxicants, or toxins. These monoclonal or polyclonal antibodies are produced in cell culture systems or in animals according to procedures known in the art. Such antibodies, or their Fab fragments, can be used, e.g. for digoxin or quinidine overdose during treatment of cardiac patients or for accidentally or intentional overdose of salicylates, theophyllines, analgesics, thyroxine-like compounds, barbiturates or tranquilizers, and for drugs of abuse.

(3) Immobilization of antibody directed toward a particular antigen, or toward an activated immunoglobulin bound to the particular antigen. For example, in patients with systemic Lupus Erythematosus, rheumatoid arthritis, myasthenia gravis, and other such immune complex diseases, removal of circulating immunocomplexes which tend to cause multiple organ damage may be of great benefit. Presently, plasmapheresis is being employed in a number of medical centers for the removal of circulating immune-complexes.

(b 4) Immobilization of "antigen" to remove "antibodies" in the circulation directed toward that antigen. One example of a disease in this category is Hashimoto's thyroiditis. In this disease, circulating antibodies against thyroglobulin deposit in the thyroid gland and cause chronic goiter; removal of circulating anti-thyroid antibodies may be accomplished with specific antihuman antibodies immobolized in multitubular cartridges. Another example is a form of insulin resistant diabetes. In this disease, high concentration of antibodies specific for insulin circulate in the blood and neutralize insulin that is administered. Selective removal of these antibodies using a bound insulin antigen in the exterior lumen of the device can be used to reduce the plasma level of those undesirable antibodies.

(5) Immobilization of bioactive proteins with affinity toward pathogenic immunoglobulins, e.g., immobilization of Protein A from *Staphylococcus aureus* for the removal of tumor associated blocking antibodies in patients with colon carcinoma, melanoma, etc. These blocking antibodies interfere with the action of regular immunologic forces of the patients against tumor cells. Blocking antibodies were shown to be a particularly important feature in certain types of cancer. Removal of blocking antibodies frees the immune system to exert its antitumor activity.

ILLUSTRATIVE EMBODIMENTS OF THE INVENTION

In this application and accompanying drawings there is shown and described a preferred embodiment of the invention and suggested various alternatives and modifications thereof, but it is to be understood that these are not intended to be exhaustive and that other changes and modifications can be made within the scope of the invention. These suggestions herein are selected and included for the purposes of illustration in order that others skilled in the art will more fully understand the invention and the principles thereof and will be able to modify it and embody it in a variety of forms, each as may be best suited to the condition of a particular case.

IN THE DRAWINGS

Figure 1:
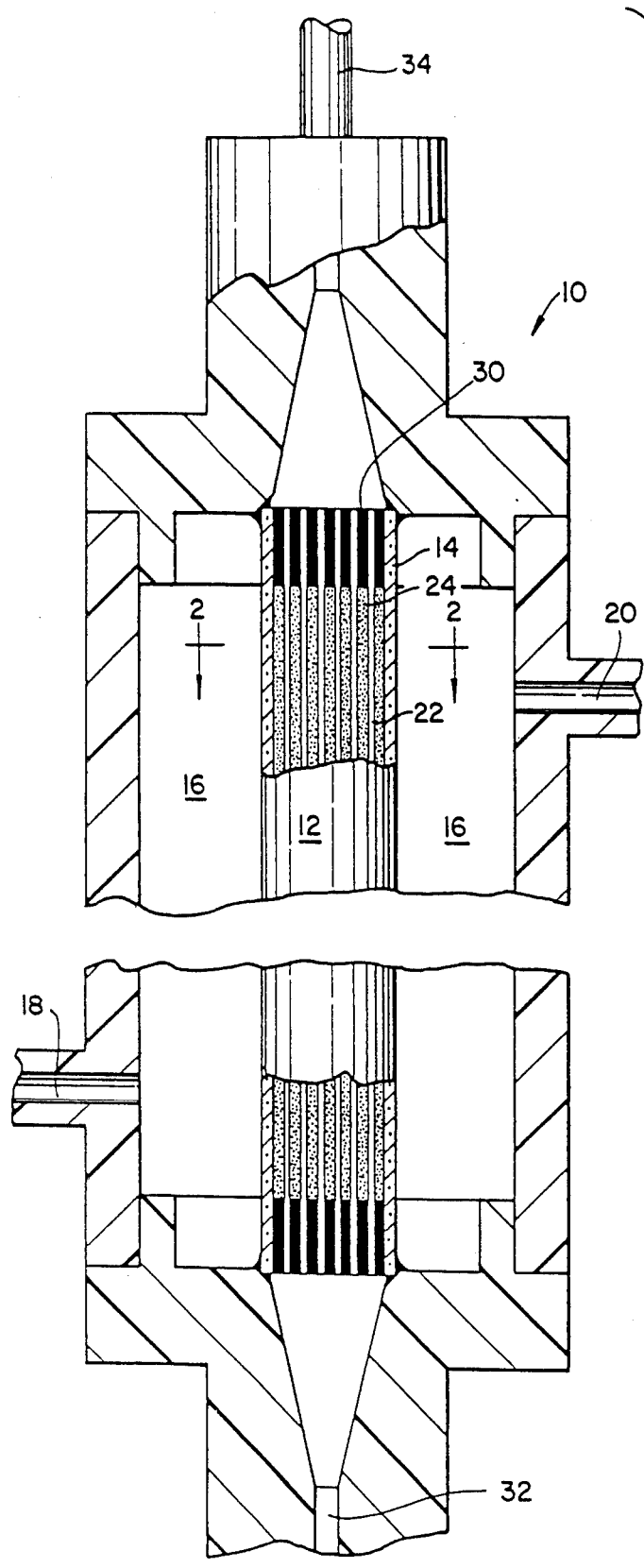
FIG. 1 is a partially schematic view of an apparatus useful in practice of the invention.
Figure 2:
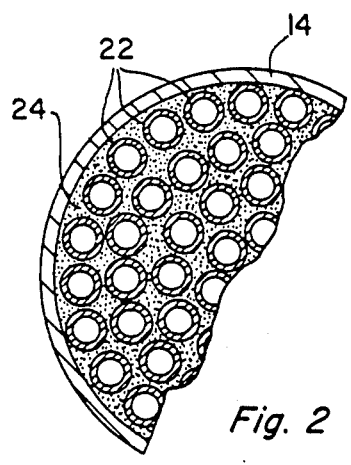
FIG. 2 is a section of FIG. 1.
Figure 3:
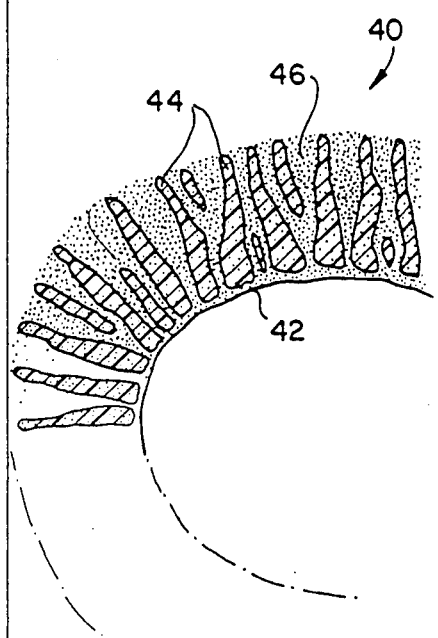
FIG. 3 is a greatly enlarged cross-section of a hollow-fiber membrane structure constructed according to the invention.

Referring to FIG. 1, it is seen that a blood processing cartridge 10 is formed of an interior, blood-processing chamber 12 formed of interior glass wall 14. Around chamber 12 is an optional exterior chamber 16 which may be utilized to control the temperature in chamber 12; the temperature of which is kept constant. A temperature-controlling fluid would be passed into chamber 16 through lower conduit 18 and passes out of the chamber through upper conduit 20. Chamber 12 contains about five hundred tubular, anisotropic, ultrafiltration membranes 22 of the type generally called "hollow-fiber membrane". In fact, these membranes are about 0.3 millimeters in inside diameter and 0.5 millimeters in outside diameter. They have interior retentive membrane walls of about 1 micron in thickness and have a nominal central conduit path of about 8 inches.

The membranes are sealed together in matrices of resin 30 at the inlet port 32 and at outlet port 34. The resin effectively seals any crossectional area which may be left between the membranes and assures all blood entering the apparatus through inlet 32 flows into the tubular membranes 32.

Immobilized on the exterior of membranes 22 is the antibody or other suitable toxin-attractive material.

EXAMPLE I

Preparing Antibodies for Immobilization

In all the cases cited below, polymers are activated, i.e. made susceptible for combining chemically with an antibody, by using processes known in the art. Several useful polymers are cited, but since the polymer acts as a carrier rather than a physiological agent, any number of other polymers may be used as substrata for carrying the antibodies. The primary requirements is that the antibody can conjugate thereto in a way which allows those molecular characteristics, which give the antibody its physiologically specific character, are left spatially free to interact with an antigen.

(1-a) A soluble, or at least dispersible, antibody is prepared by any of the number of methods including the following: An antibody suitable for any particular application is dissolved in a concentration of 50-200 mg./ml. with human serum albumin in a phosphate-buffered aqueous medium of pH 7.0, all according to procedures known in the art.

Gluteraldehyde in a concentration of 0.05-10% (depending on the protein) is added to the solution which is then incubated 12 hours at 4° C. Excess gluteraldehyde that remains in the reaction mixture is conveniently removed by addition of glycine to the solution at the end of incubation. This solution is then diafiltered through a membrane having a minimal rententivity value of 500,000 molecular weight (Dalton). The diafiltered antibody-bearing product is dissolved in saline or dialysis fluid.

(1-b) To obtain a reactive polymer, polyacrylic acid polymer (e.g. with molecular weight of about 1,000,000) is activated by the azide procedure (Erlanger BC, Isambert MF, and Nickelson AM: Biochem. Biophys. Res. Commun. 40, 70, 1970; Wilchek M, and Miron T Molecular & Cellular Biochem. 4, 181, 1974). When the finely dispersed reactive polymer is suspended in a buffered saline solution of the antibody of choice, the protein antibody will be bound to the polymer. It is important that the ratios of antibody to reactive polyester be selected to avoid excessive reaction which may result in an insoluble product. If this ratio is appropriately adjusted, the spacing of the antibody along the polymer chain will allow a binding of the antibody with the antigen without untoward steric hindrances and the antibody conjugate remains soluble.

(1-c) A copolymer of ethylene and maleic acid anhydride, for example of molecular weight 1,200,000, is partially hydrolyzed by incubating in a chamber with controlled humidity and temperature and reacted with an antibody in e.g. saline solution. Then the resulting soluble protein-polymer conjugate is used as a specific binding agent in a solution contained in the cylinder surrounding the outer walls of hollow-fiber membranes.

(1-d) Dextran (Mw 10,000-40,000 Pharmacia Fine Chemicals, Piscataway, NJ) is activated by the cyanogen bromide method (Axon et al: Nature 214, 1302, 1967) and reacted with the antibody in physiological saline media. The molecular weight of the conjugate obtained by this reaction is preferably higher than 1,000,000.

It is to be understood that when one activates a polymer, rather than starting with a pre-activated polymer of known molecular size, it is preferable to filter the activated product to remove undesired low molecular weight material which may have been created during the activation procedure.

EXAMPLE II

Selective Removal of Immunoglobulin G From Blood With Immobilized Protein A

This process for purifying blood of a living animal by passing the blood through an extracorporeal shunt device that includes an apparatus as described herein for selectively absorbing undesirable substances from the blood can have many therapeutic uses including: (a) removal of red blood cell auto-antibody for treatment of lymphocytic leukemia and auto-immune hemolytic anemia, (b) removal of tumor specific antigen for treatment of colon carcinoma and melanoma, (c) removal of multiple myeloma specific immuneglobulin G for relief of hyperviscosity in patients with multiple myeloma, etc.

As known in the art, factor Protein A can be isolated from the cell wall of *Staphylococcus aureus* Cowan I (NCTC 8530) and the activity of the protein is measured by immunodiffusion. The product so obtained specifically binds to the Fc portion of immunoglobulin G subclones 1, 2 and 4 of man.

The cellulosic hollow fibers with an ID of 200 u and inner wall thickness of 30 micrometers are potted to form a cartridge having a total tube innersurface area of 0.6 square meter. The inner walls are washed with 0.2M sodium hydroxide solution, and after drying, are perfused with a 0.1M solution of bromoacetylchloride in acetonitrile and the solution is recirculated for 2 hours at room temperature. Thereafter the inner walls are thoroughly washed with acetonitrile to remove excess reagent and dried in a nitrogen stream. Subsequently, the hollow fibers are perfused with a solution of Protein A in saline buffered with borate to maintain pH 8.5. After three hours of recirculation, the cartridge is washed extensively with saline. The solution is assayed for Protein A by immunodiffusion technique, known to the art, before and after the recirculation step in order to evaluate the degree of protein uptake by the fiber wall. Finally, the cartridge is washed with a streptomycin solution. Subsequently the cartridge is dried in a nitrogen stream, placed in a plastic bag and sealed.

Then, Protein A in a concentration of 50-200 mg/ml solution is incubated with a 0.05-10% glutaraldehyde solution in order to obtain soluble macro molecular aggregates having a molecular weight over 1,000,000. After removal of smaller species by diafiltration, the super-Protein A molecules are stored in saline solution at 4° C.

A cartridge containing 1,000 asymmetric hollow fibers having a cut-off pore-size at 500,000 Dalton MW and inner diameter of 150-200 microns is washed by pumping saline solution through the fiber walls from the outside in the "reverse" ultrafiltration mode. Thereafter a 1% solution of human serum albumin is pumped through the fiber wall in the same way in order to deposit a monomolecular layer of albumin at the porous surface of the outer side (shell side) of the tubular membrane. Thereafter the solution of super-Protein A is filtered through the walls of hollow fibers in "reverse" direction so that the crosslinked macromolecular aggregates of the biospecific binding agent are deposited directly at the shell side of the membrane or in close proximity of the membrane in the shell region. The activity of the solution before filtration and that of the filtrate leaving the lumen is assayed for Protein A. The balance gives the amount of immunological activity deposited in the cartridge. After flushing the lumen space of the hollow fiber with streptomycin and saline, the cartridge is placed into a plastic bag and sealed. Cartridges so prepared are used in extracorporeal shunts.

EXAMPLE III

A specific antibody containing cartridge for use in the extracorporeal shunt treatment of patients suffering from toxic levels of therapeutic drugs was prepared:

Hollow fiber cartridges having lengths of 250 mm and containing 535 hollow fibers were supplied by Amicon. The fiber dimensions are: I.D. 180 micron and O.D. 360 micron, and the total contact surface area in the cartridge is 750 $cm^2$.

The hollow fibers were first washed with 300 ml of distilled water is the reversed ultrafiltration mode in order to remove glycerol used to maintain wettability of the polysulfone hollow fiber membranes during storage and shipment. 500 mg. of human serum albumin (sigma) are dissolved in 250 ml 0.01M phosphate buffer, pH 7. An aliquot of 50 ml of albumin solution is pumped, in a reverse mode, through ports of the housing into what will be closed space around the hollow fiber membranes to deposit a thin albumin layer on the surface of the porous sponge structure surrounding each membrane. Thereafter a solution of digoxin antibody capable of binding 750 micrograms of digoxin is made in 50 ml of 0.01M phosphate solution, pH 7, and loaded into the cartridge in the same way as the albumin in the previous step. Thereafter, 200 ml of the albumin solution is filtered into the outerspace of the hollow fibers.

Glutaraldehyde was dissolved in 0.01M phosphate buffer, pH 7.0, in order to obtain a 1% (w/v) solution. 25 ml of the glutaraldehyde solution was pumped into the extrafiber space of the cartridge and filtered through the fiber walls into the lumen over a period of ten minutes. Then 500 ml of saline was pumped through the cartridge in the reversed ultrafiltration mode to remove unreacted glutaraldehyde.

After this treatment, the filtrate emerging from the lumen of the hollow fiber contained no traces of glutaraldehyde. The ports of the housing of the cartridge were closed with plexiglass disks and the lumen and lumen-access compartments were prepared by washing with one liter pyrogen free sterile saline solution. The cartridge, still wet with the saline solution, was sealed into a plastic container and sterilized by exposure to a gas mixture containing 7% ethylene oxide in carbon dioxide.

Sheep antidigoxin antibody was immobilized within the cartridge and exterior to the interior lumen of the hollow fiber membranes. To 150 ml., of human blood was added 11,000 nanograms per millimeter of digoxin. After connecting the antibody containing cartridge to a fluid circulating system designed to permit passage of blood into the center conduit of the multi-hollow fiber cartridge, digoxin containing blood was circulated through the system at a rate of 100 ml. per minute. Samples of blood were removed for assay of digoxin at times 0, 5, 15, 30, 45 and 60 minutes after the start of the circulation treatment. It was found that the concentration of digoxin in the circulating human blood was significantly reduced after 5 and 15 minutes of circulating through the system. After 60 minutes of treatment the digoxin concentration of the blood was reduced from the initial 11,000 nanograms per millimeter to 8,350 nanograms per millimeter which corresponds to a total of 400,000 nanograms of digoxin removed from the 150 ml. of blood.

EXAMPLE V

A drug specific antibody cartridge similar to that employed in Example III (but immobilizing a quinodine antibody) for use in the treatment of patients suffering from toxic levels of therapeutic drugs was prepared and utilized in a manner similar to that described. To 200 ml. of human blood was added 35,000 nanograms of the cardiac drug quinidine. The blood was circulated through the cartridge for one hour and samples of the blood were removed at intervals. The concentration of quinidine in the blood was found to be: Initial concentration, 174 nanograms per ml., 5 minutes treatment sample, 153 nanograms per ml, 15 minute treatment sample, 153 nanograms per ml. and 30 minute treatment sample, 148 nanograms per ml. which corresponds to a total of 5,200 nanograms of quinidine removed from the 200 ml. of blood.

EXAMPLE VI

A drug specific antibody cartridge similar to that employed in Example III, but proposed for treatment of patients suffering from toxic blood levels of drugs of abuse such as barbiturates, tranquilizers and analgesics was prepared utilizing sheep anti-barbiturate antibodies. To 200 ml. of human blood was added 8.8 mg. phenylbarbitol sodium. After treatment of the blood and analyzing the blood, it was found that the concentration of barbiturate in the blood at the various sample times was as follows: Initial, 44 micrograms per ml., and 60 minutes, 37 micrograms per ml. Therefore the cartridge removed a total of 1,400 micrograms of barbituate from the 200 ml. of blood.

EXAMPLE VII

A drug specific antibody cartridge similar to that employed in Example III prepared for treatment of patient suffering from toxic blood levels of drugs of abuse was prepared utilizing antibodies to the propoxyphene napsylate sold under the trade designation Darvon. To human blood was added propoxyphene napsylate monohydrate. After treatment of the blood, it was found that the concentration (micrograms per deciliter) of drug in the blood at the various sample times was as follows: Initial, 240, fifteen minutes, 90, thirty minutes, 10.

EXAMPLE VIII

Examples of diseases characterized by excess antibodies or antigen-antibody complexes are lupus erythematosus, rheumatoid arthritis, masthemia gravis, Factor VIII resistant hemophilic and insulin resistant diabetes. To illustrate the use of this invention in the reduction of blood antibodies and antigen-antibody complexes, a cartridge was prepared as follows:

15 g silica gel (SMR-1-89C, Davison Chemical) having mean pore and particle diameters of 300 A and 10 micron, respectively, were slurried in 100 ml of 1M hydrochloric acid and after overnight stay filtered and washed with distilled water until the filtrate was chloride free. Thereafter the silica was washed on the filter twice with 50 ml of acetone, sucked dry and kept in the oven at 100° C. for 12 hours.

After the silica was cooled to room temperature it was suspended in 60 ml of toluene containing 7.5 g of gamma-aminopropyltrimethoxysilane (Petrarch) and under stirring the suspension was heated and kept on reflux over ten hours. After the suspension was cooled to room temperature it was filtered and washed with 50 ml of toluene, 50 ml of methanol and finally with 50 ml of acetone. The product was dried in the oven at 50' C. for three hours.

0.75 g of bovine insulin Sigma were dissolved in 7.5 ml of 0.05M phosphoric acid. Then a concentrated sodium bicarbonate solution was added dropwise from a burette to the insulin solution under stirring and the pH was monitored. When the pH of the solution reached 4.5 the solution became cloudy. The addition of sodium bicarbonate continued until pH of the insulin solution reached 6.6 and thereafter the solution was stirred for five hours until it became clear again.

The aminopropylsilica described above was suspended in 50 ml of 5% (w/v) glutaraldehyde solution in 0.01M phosphate buffer, pH 7.0, and stirred for 20 minutes. Subsequently the suspension was filtered and washed with the above phosphate buffer until no glutaraldehyde was found in the filtrate.

The wet filtercake of the glutaraldehyde-treated aminopropylsilica was suspended in the above described insulin solution and stirred for 40 minutes. Thereafter the slurry was filtered and washed extensively with 750 ml 0.01M phosphate buffer, pH 7.0. The filtercake was resuspended in 50 ml of phosphate buffer, stirred for 20 minutes and centrifuged. This treatment was repeated four times and testing of the last supernatant for insulin was negative.

A hollow fiber cartridge sold under the designation "pLasmaflux P2" by Fresenius was used which has the following specifications:

| Membrane: | polysulfane |
|---|---|
| Inner diameter: | 330 micron |
| Wall thickness: | 150 micron |
| Contact surface area: | 0.5 m² |
| Priming volume lumen: | 52 ml |
| Extrafiber space: | 195 ml |

-continued

| Potting material: | Polyurethane |
|---|---|

The inside of the cartridge was first washed with one liter of saline solution to remove the glycerol used by the supplier to maintain the wettability of the asymmetric polysulfone hollow fibers. Thereafter the silica particles containing the immobilized insulin were dispersed in 500 ml saline solution and pumped into the extrafiber space of the cartridge which was gently shaken during this process. The reversed ultrafiltration of the slurry resulted in a deposition of the siliceous affinity absorbent particles on the outer shell of the hollow fibers. After a uniform distribution of the particles was accomplished, first, 1.5 L of sterile, pyrogen-free saline solution was filtered from the extrafiber space into the lumen of the hollow fibers, then 1.5 L of pyrogen-free sterile saline was pumped through the lumen compartment.

Subsequently the ports of the housing of the cartridge were closed, the cartridge was sealed into a plastic container and sterilized by ethylene oxide.

The cartridge is then connected to a circulatory system and used to purify blood from a diabetes patient with a high blood plasma insulin antibody titer. Such a treatment will cause the removal of important quantities of the insulin antibody (an "antigen-antibody") from the patient's blood.

EXAMPLE IX

An albumin containing cartridge was prepared as follows:

Hemoflow F-60 capillary dialyzer (obtained from the supplier, Freseneus of Germany) was used. The specifications of the hollow fiber cartridges are as follows:

| Membrane material: | polysulfone |
|---|---|
| Housing material: | polycarbonate |
| Potting compound: | polyurethane |
| Net weight: | 165 g |
| Inside diameter/wall thickness: | 200/40 micron |
| Surface area: | 1.25 m² |
| Priming volume blood: | 75 ml |
| Priming volume dialysate: | 230 ml |
| Flow resistance blood: | 40 mm Hg |

The protective glycerol coating of the fibers was removed by washing the cartridge with 1.5 liters of saline solution by passing the solution through it as if it were to be ultrafiltered.

A quantity of 10 g of bovine serum albumin, Fraction V Powder (sigma), were dissolved in 1 Liter of 0.01M phosphate buffer, pH 7.0, and pumped through the two ports of the housing into the hollow fiber cartridge in order to deposit the protein in the spongelike outer shell of the polysulfone fibers by a filtration in the reverse direction. The flow rate was 10 ml per minute and slight vacuum was applied to both ends of the lumen compartment of the cartridge.

Glutraldehyde (Fisher) was dissolved in 500 ml of 0.01M phosphate buffer, pH 7, in order to obtain a 1% (w/v) glutaraldehyde solution.

After the albumin solution was filtered into the hollow fibers the glutaraldehyde solution was pumped into the cartridge in the same way. The flow rate was 15 ml/minute. Upon contact with the glutaraldehyde, the bovine serum albumin deposited at the outer surface of the capillary membrane proper, i.e. in the porous shell, became crosslinked and thereby immobilized at the polysulfone surface.

The cartridge was washed with 1.5 L of pyrogen-free and sterile saline solution first in the reversed ultrafiltration mode then through the lumen compartment. Thereafter the cartridge with hollow fibers still wetted by saline was sealed into a plastic container and sterilized by ethylene oxide.

The albumin cartridge was connected to a circulating system and 100 ml. of blood obtained from a patient suffering from hyperbilirubinemia was pumped through the system. The initial concentration of total bilirubinemia in the blood was 29 milligrams per deciliter blood. After treatment for 100 minutes the concentration of bilirubinemia has decreased to 19 milligrams per deciliter which corresponds to a total of 10 milligrams of bilirubin removed from the 100 ml. of blood.

EXAMPLE X

A column was prepared, according to the procedure of Example III but using a specific antibody to 1-thyroxine as the immunoreactive agent on the exterior side of a membrane device as described above. The membranes were of the nominal 10,000-Dalton cutoff type. Into a quantity of 175 ml of human blood, was added 72 micrograms of Na 1-thyroxine. The initial concentration in the blood was 0.41 micrograms per milliliter. After 60 minutes of treatment, the concentration had dropped to 0.348 micrograms per ml. Thus 11 micrograms of Na 1-thyroxine was removed from the 175 ml of blood.

In appraising the advantages of the invention, it appears that the particularly beneficial properties are achieved by providing a steady-state diffusion process across the wall of the membrane whereby a high concentration gradient is maintained across the membrane by the placement of the antigen-attracting material deposited on the exterior of the membrane. Because the volume of the container of the membranes is both closed and of very limited volume, there are only trivial quantities of relatively small blood chemicals lost during the first time of operation of the cartridge. Thereupon, a diffusion equilibrium is established with respect to such chemicals and no further net loss of such chemicals occurs.

It will be apparent that the optimum size of the membrane pores will differ from application-to-application, but in no event will they be large enough to admit the formed elements of the blood.

It is also to be noted that bacteria can also be attracted across the membrane and immobilized outside the blood stream.

The antibody may be bound or unbound. It may be in the from of an oil-in-water emulsion. It may be bound to another molecule or to the surface of the membrane, e.g. the exterior of the hollow-fiber tube. It may be linked to a spacer molecule. Such spacers are usually the length of several carbon atoms, say up to about 20 but often about 4 to 12 carbons in length.

Depending on the nature of the antigen to be removed, the nominal membrane pore size can be quite large, but never large enough to admit blood cells. Nominal pore sizes (globular-molecule separation test known in the art) of 50,000 are effective in the antibody applications disclosed herein but antigen-antibody-type toxins require pore sizes of up to about 50 millimicrons in nominal diameter. For some smaller antibodies, a pore size of only about 10,000 daltons is acceptable. In the preferred embodiments of the invention, not only will blood cells be prevented from passing through the membrane, but all formed elements of the blood including all platelets, biocytes and thrombocytes will be maintained exclusively on the barrier side of the membrane.

Mixtures of antibodies can usually be used in a substantially additive way. In such a case the removal of a plurality of antigens appears to be essentially non-competitive.

Albumin, besides being an easily-immobilized collector of some toxins from the blood, is also a good material by which to bind or immobilize other antibodies. For example, antidigoxin antibodies can be bound to albumin. Sometimes it is desirable to polymerize antibodies for immuno-scavenging use. Anti digoxin antibodies are an example of this. By doing so, one can allow use of larger effective diffusion pores in the membrane without danger of back diffusion of the immunoscavenging means.

It is also to be understood that the following claims are intended to cover all of the generic and specific features of the invention herein described and all statements of the scope of the invention which might be said to fall therebetween.

What is claimed is:

1. A process for removing antigens from blood fluid comprising the steps of (1) immobilizing a specific immunoreactive scavenging means for said antigen within a porous exterior surface of said membrane, (2) passing an antigen-bearing blood fluid along a retentive-barrier side of an anisotropic membrane the barrier layer of which will not allow passage of the blood cells, (3) assuring a unidirectional diffusion process is the only steady-state process for carrying any other blood components through said membrane by maintaining the porous side of said membrane in a closed container of constant volume, and (4) utilizing said scavenging means to maintain a concentration gradient of said antigen across said membrane and to achieve an improved capture rate of said antigen by said immunoreactive scavenging means.

2. A process as defined in claim 1 wherein said membrane barrier surface is in the form of the interior surfaces of a plurality of closely spaced tubes and wherein said agent is positioned within the porous exterior portion of said tubes.

3. A process as defined in claim 2 wherein said antigen is digoxin.

4. A process as defined in claim 2 wherein said antigen is a barbiturate.

5. A process as defined in claim 2 wherein said antigen is propoxyphene napsylate.

6. A process as defined in claim 2 wherein said antigen is an antigen antibody complex.

7. A process as defined in claim 6 wherein said antigen antibody complex is an insulin antibody.

8. A process as defined in claim 2 wherein said antigen is quinidine.

9. A process as defined in claim 2 wherein said antigen is bilirubin and said antibody is albumin.

10. A process as defined in claim 2 wherein said antigen is immunoglobulin G.

11. A process as defined in claim 2 wherein said antigen is a bacteria.

12. A process as defined in claim 2 wherein said antigen is 1-thyroxin.

13. A process as defined in claim 1 wherein said antigen is about 100,000 daltons and wherein said immunoreactive scavenging agent is attached to said membrane via a molecular space segment.

14. A process as defined in claim 13 wherein said spacer material is formed of albumin.

15. A process as defined in claim 13 wherein said immobilized scavenging agent is albumin.

16. A process as defined in claim 1 wherein said immunoreactive scavenging agent is in the form of an antibody which is chemically reacted to a high-molecular weight substrate to inhibit diffusion from the porous portion of said membrane.

17. A process as defined in claim 16 wherein said high molecular weight substrate is silica gel or dextran or a polymer formed of said scavenging agent.

18. A process as defined in claim 16 wherein said immobilized scavenging agent is albumin.

* * * * *

UNITED STATES PATENT AND TRADEMARK OFFICE
CERTIFICATE OF CORRECTION

PATENT NO. : 4,714,556

DATED : 22 December 1987

INVENTOR(S) : Clara M. Ambrus and Csaba Horvath

It is certified that error appears in the above—identified patent and that said Letters Patent is hereby corrected as shown below:

Column 10, Line 26 "diabetes" should read --diabetic--;

Column 11, Line 67 "50" should read --500--.

Signed and Sealed this

Seventeenth Day of May, 1988

Attest:

DONALD J. QUIGG

Attesting Officer

Commissioner of Patents and Trademarks